United States Patent [19]

Slaugh

[11] 4,375,424

[45] Mar. 1, 1983

[54] CATALYST FOR THE PREPARATION OF DIMETHYL ETHER

[75] Inventor: Lynn H. Slaugh, Houston, Tex.

[73] Assignee: Shell Oil Company, Houston, Tex.

[21] Appl. No.: 313,420

[22] Filed: Oct. 21, 1981

[51] Int. Cl.$^3$ .................... B01J 21/04; B01J 23/06; B01J 23/72
[52] U.S. Cl. ..................................... 252/463; 518/713
[58] Field of Search ................. 252/463, 475; 518/713

[56] References Cited

U.S. PATENT DOCUMENTS 4,011,275  3/1977  Zahner .............................. 518/714
4,111,847  9/1978  Stiles ................................. 252/463
4,177,167  12/1979  Manara et al. .................. 252/455 R Primary Examiner—W. J. Shine

[57] ABSTRACT

A catalyst and a process for producing dimethyl ether from syngas which catalyst comprises copper and zinc supported on a gamma alumina with a surface area of about 150–500 m$^2$/g and which has been calcined at a temperature of about 400°–900° C. and reduced at a temperature of about 100°–275° C. and wherein said catalyst has a sodium content of less than about 700 ppm.

3 Claims, No Drawings

CATALYST FOR THE PREPARATION OF DIMETHYL ETHER

BACKGROUND OF THE INVENTION

1. Field of the Invention

This invention relates to a process for the conversion of syngas to dimethyl ether and the catalysts used therein.

2. Background of the Invention

There are many catalysts that are known for the conversion of syngas to methanol. However, thermodynamic considerations limit the syngas conversion per pass to the 20-30% range for methanol production. Thus, substantial amounts of costly syngas recycled are required to produce methanol. On the other hand, such thermodynamic limits do not exist when converting syngas to dimethyl ether, and, hence, very deep conversions are possible when preparing dimethyl ether. Dimethyl ether is a very useful chemical intermediate for the conversion to other useful products. In principle then, dimethyl ether could be a more attractive intermediate from a cost input than is methanol for the production of other products. U.S. Pat. No. 4,098,809, issued July 4, 1978, generally discloses the use of a copper/zinc/chromium catalyst combined with alumina for the conversion of a mixture of CO, $CO_2$ and $H_2$, wherein the quantity of CO is in excess of the stoichiometric value, to dimethyl ether. U.S. Pat. 4,177,167, issued Dec. 4, 1979 discloses the use of oxides of chromium, lanthanum, manganese, copper, zinc and aluminum oxide which have been stabilized by means of an organo orthosilicate compound.

SUMMARY OF THE INVENTION

This invention relates to the catalysts and the accompanying process for converting syngas into dimethyl ether with substantial yields. Particularly, it relates to a catalyst and process wherein the carbon monoxide which is converted to hydrocarbons is converted with a selectivity to dimethyl ether of greater than about 80 mol percent. The catalyst used in this process comprises from about 2% to about 8% by weight of copper and from about 2% to about 8% by weight of zinc supported on an alumina support having a surface area ranging from about 150 to about 500 $m^2/g$, wherein said catalyst is prepared by impregnating said alumina support with a solution of copper and zinc salts, calcining the impregnated support in an oxidizing or neutral atmosphere at a temperature ranging from about 400° C. to about 900° C. and then contacting the calcined material with a reducing atmosphere at a temperature ranging from about 100° C. to about 275° C. and wherein further said catalyst has a sodium content of less than about 700 ppm. Catalysts prepared in such fashion are more active and more selective than catalysts with higher or lower metal loadings, catalysts which utilize supports having lower surface areas, or catalysts containing higher concentrations of sodium.

DESCRIPTION OF THE PREFERRED EMBODIMENTS

There are several aspects to the preparation of the catalyst used in the instant invention that are crucial to its operation. When the metal loadings on the catalysts are too low, the conversion of the syngas declines. On the other hand, catalysts which retain a relatively high metal content tend to produce more methanol. Thus, preferably, the catalysts of the instant invention contain copper ranging from about 2% to about 5% by weight, basis total catalyst, and more preferably ranging from about 3% to about 7% by weight. The zinc ranges from about 2% to about 8% by weight of the total catalysts and preferably from 3% to about 7% by weight.

The support that is utilized to prepare the catalysts of the instant invention is an alumina support, preferably a gamma alumina support. Other supports such as silica and silica-aluminas are unsatisfactory. The support surface area is critical to the catalysts of the instant invention and must range from about 150 to about 500 $m^2/g$.

The preparative conditions involving calcination and reduction are also found to be critical. The first step in the preparation of the catalyst is to impregnate the alumina support with solubilized salts of copper and zinc. The salts must be soluble in a suitable solubilizing media, either organic or inorganic. Water is a preferred solubilizing media. Suitable salts are, for example, chlorides, bromides, nitrates, acetates, lactates and the like. Nitrates are a preferred salt. The impregnation of the support may be carried out in one step utilizing both metals dissolved in a solution, or it may be carried out in a multi-step process, using each of the metal salts dissolved in individual impregnating solutions, with the impregnation taking place sequentially. The impregnating step(s) may be repeated one or more times to provide the optimum metal loading. A preferred impregnating process is the so-called "dry impregnation technique" wherein just a sufficient amount of impregnating solution is used such that all the pore volume in the carrier is filled and no excess solution is left after impregnation. The next step is to dry and calcine the impregnated material. The drying and calcining can be carried out in individual steps. For example, drying can be carried out at temperatures up to about 150° C. followed by the calcining step at temperatures ranging from about 400° C. to about 900° C. Preferably, the drying and calcining are carried out in one continuous step, heating the material slowly through the low temperature ranges to dry the material and then raising the temperature to the calcining conditions. The purpose of the calcining is to convert the soluble metal salts into what is believed to be oxides upon the support material. Calcining is carried out in a neutral or oxidizing atmosphere, air being the preferred atmosphere. Nitrogen is also a suitable alternative atmosphere. Catalysts that are calcined at too low of a temperature, i.e. below about 400° C., do not provide for sufficiently active catalyts. Catalysts which calcined at too high of a temperature, i.e. above about 900° C., will have a reduced surface area and also a reduced activity. The drying times are not critical and depend upon temperatures. These times are readily determined by simple experimentation. Five minutes to 10 hours are usually sufficient, although longer times are acceptable.

To provide for an active and selective catalyst the calcined material must be reduced by heating in a suitable reducing atmosphere. While not wishing to limit this invention, it is believed that the reduction process must at least partially reduce the copper from the +2 oxidation state to the lower oxidation states but must not be so severe as to reduce the zinc from the +2 state to the lower oxidation state. Reducing conditions range from about 100° C. to about 275° C. Suitable reducing atmospheres are, for example, hydrogen atmospheres and carbon monoxide atmospheres. Hydrogen is the preferred reducing medium.

It has also been found that the sodium content of the catalyst material is critical. The sodium content of the final catalyst material must be less than about 700 ppm. There are several aspects of the preparative technique that must be monitored carefully in order to minimize the sodium content. Many commercially available alumina supports are prepared from sodium aluminates, and special techniques must be carried out in their preparation in order to maintain the sodium concentration at relatively low levels. Supports whose sodium concentrations moderately exceed those limits required for the preparation of the instant catalyst can have their sodium limits lowered by suitable acid washing. Another way that unsuitably high sodium contents are obtained is by contamination from the impregnating solutions. Suitable impregnating salts should be chosen so as to minimize sodium levels in the impregnating solutions.

The catalysts of the instant invention are used in typical fashion, for example, in packed beds or in fluidized beds. In a typical operation, a process stream containing hydrogen and carbon monoxide is passed over the catalyst bed at a temperature ranging from about 250° C. to about 325° C. and at a pressure ranging from about 40 to about 300 atmospheres. The ratios between the reagents are not particularly critical with molar ratios of $CO/H_2$ between about 1:10 and about 3:1 being preferable. The gaseous hourly space velocity can be varied, preferentially, between about 1,000 hours$^{-1}$ and about 10,000 hours$^{-1}$, but also with higher spacial velocities satisfactory results can be obtained. The reaction mixture can also contain gases which are inert to the reaction concerned, such as, for example, nitrogen. Carbon dioxide may also be present.

Preparation of the catalysts used in the instant invention and the utilization of these catalysts in the instant process will be further described below by the following illustrative embodiments which are provided for illustration and are not to be construed as limiting the invention.

ILLUSTRATIVE EMBODIMENTS

Catalyst Preparation

The following example describes a typical preparation of a catalyst used in the instant process.

7.2 Grams of copper nitrate (24.4 m moles) and 7.8 grams of zinc nitrate (26.22 m moles) are dissolved in water to make 30 ml volume and added to 30 g of 16–30 mesh alumina (CCI lot 311 SB 157). After 0.5 hr., the material is loaded into a vycor tube, an air stream of 500 ml/min is passed downward and a temperature program is initiated with an eight minute period to 100° and a 120 minute period to 500°.

Analysis of the catalyst shows it to contain about 6.1% w of copper, about 4.8% w of zinc and about 160 ppm of sodium. The catalyst is then diluted (50% by volume) with inert silicon carbide chips (Aluxite) and placed in a tubular flow reactor for activation. Hydrogen at 1 atmosphere is passed over the catalyst at a space velocity of 80 ml hydrogen flow per ml of catalyst. The activation temperature is programmed from 100° C. to 270° C. over a 2 hr. period. The catalyst is then cooled to ambient conditions and is now ready for testing.

PROCESS

A series of catalysts both according to this invention and not according to this invention (for comparative purposes) are prepared as described above. In a test of these catalyts, about 5 grams of catalyst material diluted (50% by volume) with inert silicon carbide chip are loaded into a tubular flow reactor and heated to the appropriate reaction temperature. Carbon monoxide and hydrogen in a molar ratio of about 1:1 are fed into the reactor at a pressure of about 1700 psig and a gaseous hourly space velocity of about 3,000. The products of the reactor are analyzed by gas chromatography. The results are shown in Table I below.

TABLE I

DIMETHYL ETHER FROM SYNGAS: SUPPORT EFFECT
PRESSURE = 1700 PSIG
GHSV = 3000

| Example | CATALYST[a] Cu/Zn/Support | Na, ppm | % WT Metal[n] | TEMP. °C. | CO[g] CONV. % | MOLAR SELECTIVITY, % (excluding $CO_2$) | | | | | |
|---|---|---|---|---|---|---|---|---|---|---|---|
| | | | | | | $CH_4$ | $C_2$–$C_7$ | $Me_2O$ | MeOH | EtOH | $C_3OH + C_4OH$ |
| 1 | Kaiser KA-201 $Al_2O_3$[b] | 600 | 5 Cu, 5 Zn | 292–305 | 55.2 | 1.8 | 3.0 | 83.7 | 11.6[c] | — | — |
| 2 | Reynolds RA-1 $Al_2O_3$[e] | 4700 | 5 Cu, 5 Zn | 272–280 | 42.9 | 0.6 | 1.0 | 3.6 | 85.4 | 5.5[d] | 3.9[d] |
| | | | | 292–298 | 40.0 | 1.8 | 3.4 | 19.6 | 61.3 | 7.1[d] | 6.9[d] |
| 3 | Catapal $Al_3O_3$[f] | 40 | 5 Cu, 5 Zn | 274–282 | 38.1 | 1.7 | 1.4 | 90.2 | 6.8 | — | — |
| | | | | 297–307 | 56.4 | 2.6 | 1.7 | 92.0 | 3.7 | — | — |
| 4 | SCS-59 $Al_2O_3$[h] | 600 | 5 Cu, 5 Zn | 298 | 19.6 | 0.5 | 4.4 | 13.1 | 80.1 | 1.9 | — |
| 5 | SCS-250 $Al_2O_3$[i] | 600 | 5 Cu, 5 Zn | 297–303 | 70.4 | 0.6 | 0.8 | 94.0 | 4.8 | — | — |
| 6 | CCI $Al_2O_3$[j] | 160 | 5 Cu, 5 Zn | 293–307 | 64.5 | 1.1 | 0.4 | 94.2 | 4.4 | — | — |
| 7 | Norton $Al_2O_3$[k] | 51 | 5 Cu, 5 Zn | 292–298 | 68.1 | 0.4 | 0.4 | 94.4 | 4.8 | — | — |
| 8 | Davison 57 $SiO_2$[l] | 750 | 5 Cu, 5 Zn | 294–300 | 13.5 | 1.2 | 1.2 | 9.5 | 86.6 | 1.4 | — |
| 9 | $SiO_2·Al_2O_3$[m] | 400 | 5 Cu, 2.5 Zn | ~300 | 5.8 | 6.2 | 12.8 | 80.5 | 0.7 | — | — |
| 10 | CCI $Al_2O_3$[o] | 4300 | 5 Cu, 5 Zn | 293–298 | 43.3 | 1.4 | 2.3 | 35.5 | 60.8 | — | — |

TABLE I-continued

DIMETHYL ETHER FROM SYNGAS: SUPPORT EFFECT
PRESSURE = 1700 PSIG
GHSV = 3000

| Example | CATALYST[a] Cu/Zn/Support | Na, ppm | % WT Metal[n] | TEMP. °C. | CO[g] CONV. % | MOLAR SELECTIVITY, % (excluding CO$_2$) |||||| 
|---|---|---|---|---|---|---|---|---|---|---|---|
| | | | | | | CH$_4$ | C$_2$-C$_7$ | Me$_2$O | MeOH | EtOH | C$_3$OH + C$_4$OH |
| 11 | CATAPAL Al$_2$O$_3$[p] | 20,000 | 5 Cu, 5 Zn | ~300 | 36.7 | 2.0 | 2.7 | 2.8 | 78.7 | 5.8 | 8.1 |

Footnotes to Table I
[a] Catalysts were prepared by impregnation of the supports with an aqueous solution of the metal nitrates followed by calcination in air to 500° C. and a subsequent H$_2$ reduction from 100–270° C.
[b] Kaiser KA-201 Al$_2$O$_3$: 365 m$^2$/g; Na, 600 ppm.
[c] Number may be on the low side.
[d] Contained some esters.
[e] Reynolds RA-1 Al$_2$O$_3$: 263 m$^2$/g; Na, 4700 ppm; Fe$_2$O$_3$, 1800 ppm.
[f] Catapal Al$_2$O$_3$: 348 m$^2$/g; Na, 40 ppm
[g] Does not include CO converted to CO$_2$.
[h] Rhodia's SCS-59 Al$_2$O$_3$: 60 m$^2$/g; Na, 600 ppm. (Rhodia obtained from Pechiney.)
[i] Rhodia's SCS-250 Al$_2$O$_3$: 250 m$^2$/g; Na, 600 ppm. (Rhodia obtained from Pechiney.)
[j] CCI Al$_2$O$_3$: 250 m$^2$/g; Na, 160 ppm.
[k] Norton Al$_2$O$_3$: 218 m$^2$/g; Na, 51 ppm.
[l] Davison Grade 57 SiO$_2$: 300 m$^2$/g; Na, 750 ppm.
[m] Davison 980-25 SiO$_2$.Al$_2$O$_3$: 325 m$^2$/g; 400 ppm.
[n] These are estimated % metal loadings; the analytical values may differ by a few tenths of a percentage unit.
[o] CCI Al$_2$O$_3$: 250 m$^2$/g; Na, 4300 ppm added as NaOH.
[p] CATAPAL Al$_2$O$_3$: 348 m$^2$/g; Na, 20,000 ppm added as NaOH.

Examples 1, 3, 5, 6, and 7 are catalysts prepared according to the instant invention. Examples 2, 4, 8, 9, 10, and 11 are comparative materials. The catalyst of Example 2 contains sodium concentrations outside the limits of the instant invention and produces mainly alcohols. The catalyst of Example 4 has a surface area below the limits of the instant invention and again produces primarily alcohols. The catalyst of Example 8 is supported on a silica catalyst rather than an alumina catalyst and also produces primarily alcohols. The catalyst of Example 9 is supported on a silica-alumina catalyst rather than on a gamma alumina catalyst and shows extremely low activities. The catalysts of Examples 10 and 11 contain extremely high sodium concentrations. These catalysts were prepared by taking the catalysts of Example 6 and 3 and impregnating with solutions of sodium hydroxide. After impregnation the materials were subsequently calcined at a temperature of about 500° C. and reduced in hydrogen at a temperature of about 270° C. As can be seen the yield of methanol increased dramatically at the expense of dimethyl ether.

Additional catalysts were prepared according to the instant invention with different metal concentrations and tests as above. The results are shown in Table II below.

TABLE II

DIMETHYL ETHER FROM SYNGAS: METAL LOADING EFFECT
PRESSURE = 1700 PSIG
GHSV = 3000
Na, ppm = 600

| Example | CATALYST[a] | % WT Metal[b] | TEMP. °C. | CO[c] CONV. % | MOLAR SELECTIVITY, % (excluding CO$_2$) |||||| 
|---|---|---|---|---|---|---|---|---|---|---|
| | | | | | CH$_4$ | C$_2$-C$_7$ | Me$_2$O | MeOH | EtOH | C$_3$OH + C$_4$OH |
| 12 | Cu/Zn/KA-201 Al$_2$O$_3$[d] | 2.5 Cu, 2.5 Zn | 300 | 33.6 | 3.1 | 8.0 | 85.2 | 3.7 | — | — |
| 13 | Cu/Zn/KA-201 Al$_2$O$_3$[d] | 5 Cu, 2.5 Zn | 288–299 | 66.2 | 2.1 | 0.2 | 82.7 | 15.0 | — | — |
| | | | ~305 | 64.4 | 3.1 | 0.8 | 93.4 | 2.6 | — | — |
| | | | 338–346 | 66.9 | 15.5 | 1.9 | 80.8 | 1.9 | — | — |
| 1 | Cu/Zn/KA-201 Al$_2$O$_3$[d] | 5 Cu, 5 Zn | 292–305 | 55.2 | 1.8 | 3.0 | 83.7 | 11.6[e] | — | — |
| 14 | Cu/Zn/KA-201 Al$_2$O$_3$[d] | 7.5 Cu, 5 Zn | ~300 | 67 | 3.0 | 4.9 | 81 | 11 | — | — |
| 15 | Cu/Zn/KA-201 Al$_2$O$_3$[d] | 7.5 Cu, 7.5 Zn | 268–273 | 41.2 | 1.4 | 0.9 | 23.3 | 74.5 | — | — |
| | | | 293–300 | 56.7 | 2.6 | 3.5 | 82.4 | 11.5 | — | — |

[a] See footnote [a] of Table I for catalyst preparation procedures.
[b] These are estimated % wt metal loadings; the analytical values may differ by a few tenths of a percentage unit.
[c] Does not include CO converted to CO$_2$.
[d] Kaiser KA-201 Al$_2$O$_3$: 365 m$^2$/g; Na, 600 ppm.
[e] Number may be on the low side.

Further examples are provided showing the influence of pressure as well as the influence of catalyst activation techniques on dimethyl ether yields. These results are shown in Table III below. As is noted, when the pressure is lowered, the amount of methane appears to increase slightly (compare Example 16 with Example 17 and also see Example 18 as compared to Example 19). As would be expected, conversion of CO decreases in going from 1700 psig to 900 psig at a GHSV of 3,000; however, the selectivities to dimethyl ether were exceptional (Examples 18 and 19). Table III also illustrates the importance of activation conditions for the catalysts. For example, reduction of the catalysts at 500° C. (Example 20) substantially lowers its activities relative to a catalyst reduced up to 270° C. (Example 16). When the calcination takes place at only 340° C., the activity is lower (Example 22).

TABLE III
DIMETHYL ETHER FROM SYNGAS

| Example | CATALYST[a] | % WT Metal[b] | TEMP °C. | PRESS. PSIG | GHSV | CO[c] CONV. % | MOLAR SELECTIVITY, % (excluding CO$_2$) | | | | | |
|---|---|---|---|---|---|---|---|---|---|---|---|---|
| | | | | | | | CH$_4$ | C$_2$-C$_7$ | Me$_2$O | MeOH | EtOH | C$_3$OH + C$_4$OH |
| INFLUENCE OF PRESSURE | | | | | | | | | | | | |
| 16 | Cu/Zn/KA-201 Al$_2$O$_3$[d] | 5 Cu, 2.5 Zn | 288–299 | 1700 | 3000 | 66.2 | 2.1 | 0.2 | 82.7 | 15.0 | — | — |
| 17 | Cu/Zn/KA-201 Al$_2$O$_3$[d] | 5 Cu, 2.5 Zn | 297–300 | 900 | 3000 | 39.4 | 6.0 | 0.8 | 89.0 | 4.2 | — | — |
| 18 | Cu/Zn/CCI Al$_2$O$_3$[e] | 5 Cu, 5 Zn | 293–307 290–300 | 1700 900 | 3000 3000 | 64.5 33.8 | 1.1 1.5 | 0.4 — | 94.2 98.5 | 4.4 0.1 | — — | — — |
| 19 | Cu/Zn/Norton Al$_2$O$_3$[f] | 5 Cu, 5 Zn | 292–298 292–300 | 1700 900 | 3000 3000 | 68.1 42.2 | 0.4 0.8 | 0.4 0.7 | 94.4 97.0 | 4.8 1.5 | — — | — — |
| INFLUENCE OF CATALYST ACTIVATION CONDITIONS | | | | | | | | | | | | |
| 20 | Cu/Zn/KA-201 Al$_2$O$_3$[d] H$_2$ reduced to 500° C. | 5 Cu, 2.5 Zn | 295–302 | 1700 | 3000 | 43.4 | 3.2 | 1.3 | 88.5 | 7.1 | — | — |
| 21 | Cu/Zn/SiO$_2$. Al$_2$O$_3$[g] | 5 Cu, 2.5 Zn | 300 | 1700 | 3000 | 5.8 | 6.2 | 12.8 | 80.5 | 0.7 | — | — |
| 22 | Cu/Zn/KA-201 Al$_2$O$_3$[d] Calcined only to 340° C., H$_2$ redn. to 270° C. | 5 Cu, 2.5 Zn | 300–302 | 1700 | 3000 | 38.0 | 2.6 | 0.7 | 89.9 | 6.7 | — | — |

Footnotes for Table III
[a] See footnote $a$ of Table I for catalyst preparation procedures. However, in Example 20 the H$_2$ reduction was up to 500° C.
[b] These are estimated % wt metal loadings based on preparative techniques; the precise analytical values may differ by a few tenths of a percentage unit.
[c] Does not include CO converted to CO$_2$.
[d] Kaiser KA-201 Al$_2$O$_3$: 365 m$^2$/g; Na, 600 ppm.
[e] CCI Al$_2$O$_3$: 250 m$^2$/g; Na, 160 ppm.
[f] Norton Al$_2$O$_3$: 218 m$^2$/g; Na, 51 ppm.
[g] Davison 980-25 SiO$_2$.Al$_2$O$_3$: 325 m$^2$/g.

I claim:
1. A catalyst for the production of dimethyl ether in high yield from carbon monoxide and hydrogen comprising from about 2% to about 8% by weight copper and from about 2% to about 8% by weight of zinc supported on an alumina support having a surface area ranging from about 150 to about 500 m$^2$/g, wherein said catalyst is prepared by impregnating said alumina support with a solution of solubilized salts of copper and zinc, calcining the impregnated support in an oxidizing or neutral atmosphere at a temperature ranging from about 400° C. to about 900° C. and then contacting the calcined support with a reducing atmosphere at a temperature ranging from 100° C. to about 275° C. and wherein said catalyst has a sodium content of less than about 700 ppm.

2. The catalyst of claim 1 wherein the support is a gamma alumina.

3. The catalyst of claim 1 or 2 wherein the copper ranges from about 3% to about 7% by weight and the zinc ranges from about 3% to about 7% by weight.

* * * * *